United States Patent [19]

Brandt et al.

[11] Patent Number: 4,826,776
[45] Date of Patent: May 2, 1989

[54] METHOD FOR DETERMINING HYALURONIC ACID, AND A REAGENT KIT FOR SAID METHOD

[75] Inventors: Ragnhild K. Brandt, Knivsta; Margareta E. Hedlöf, Rimbo, both of Sweden

[73] Assignee: Pharmacia AB, Uppsala, Sweden

[21] Appl. No.: 124,589

[22] Filed: Nov. 24, 1987

[30] Foreign Application Priority Data

Dec. 8, 1986 [SE] Sweden ................................ 8605270

[51] Int. Cl.⁴ .................. G01N 33/544; G01N 33/548
[52] U.S. Cl. ..................................... 436/501; 436/518; 436/529; 436/815
[58] Field of Search ................ 436/501, 518, 529, 815

[56] References Cited

U.S. PATENT DOCUMENTS 4,704,356 11/1987 Thonar ........................... 436/811 X

OTHER PUBLICATIONS

Tengblad, A., Biochimica et Biophysica Acta, 578, 281–289, (1979).
Delpech, B. et al., Anal. Biochem., 149, 555–565 (1985).

*Primary Examiner*—Sidney Marantz
*Attorney, Agent, or Firm*—Fred Philpitt

[57] ABSTRACT

Method in determining hyaluronic acid by means of inhibition technique where in addition to the hyaluronic acid of the sample (analyte) a first reactant possessing hyaluronic acid structure (reactant (1), derivatized hyaluronic acid) and a second reactant possessing a hyaluronic acid binding structure (reactant (2)) are reacted with one another to form a complex in which reactants (1) and (2) are held together due to biospecific affinity. The complex is indicated by the use of a label that is attached covalently to one of the reactants or indirectly by the use of an antibody reactive with said complex. The features characteristic of the method are that (i) reactant (2) is a reactant possessing the hyaluronic acid binding structure of cartilage proteoglycan and (ii) the reaction of reactants (1) and (2) with each other is performed (a) at a pH within the range of 5.8–7.3, this pH having been obtained in that externally added buffering components (acid - base pair) having a buffer capacity within the said range have a total concentration exceeding 0.04 M in the reaction mixture, and (b) at a temperature in the range of $+0°$ C. to $27°$ C.

5 Claims, No Drawings

METHOD FOR DETERMINING HYALURONIC ACID, AND A REAGENT KIT FOR SAID METHOD

Hyaluronic acid is a polysaccharide of a structure comprising a straight unbranched polysaccharide chain with alternating units of N-acetyl glucosamine and glucuronic acid. Hyaluronic acid is present ubiquitously in various types of biological material and is recoverable from bacteria and animals (including both vertebrates and invertebrates). In man, hyaluronic acid is to be found in high concentrations in e.g. umbilical cords, vitreous humor of the eyes, cartilage and synovial fluid. Small amounts of hyaluronic acid can be demonstrated in inter alia CSF, lymph, urine and serum. Levels in the blood, serum and plasma may be extremely low, and have been shown to increase concomitantly with ageing, rheumatoid arthritis and many liver diseases (liver cirrhosis). In this latter case, levels 25 times higher than normal have been shown to occur. For a review see e.g. A. Engström/Laurent, Thesis (3).

Various methods are available or have been suggested for determining low levels of hyaluronic acid. It was considered to be a difficult task to utilize immunological techniques with the aid of antibodies directed against hyaluronic acid, in the first place because hyaluronic acid must be regarded as being a substantially non-immunogenic substance (cp its biological ubiquity). The great advance towards measuring low levels of hyaluronic acid was made only when it was discovered that there are proteins capable of exclusively binding to the hyaluronic acid by way of biospecific affinity. Up to now, proteoglycan and/or so-called link protein, both from cartilage, or hyaluronectin from brain have been employed as substitutes for antibodies directed against hyaluronic acid. Cartilage proteoglycan and link protein are believed to contain one binding site each for hyaluronic acid, whereas hyaluronic acid itself is believed to possess a plurality of binding sites, due to its large number of repetitive structures. Morever cartilage proteoglycan and link protein are believed to be capable of binding to each other. The proteoglycan region containing the hyaluronic acid binding structure is usually called "HABr". This term "HABr" will henceforth be used (unless otherwise stated) for intact cartilage proteoglycan or fragments thereof that comprises the hyaluronic acid binding structure of cartilage proteoglycan.

By means of the first hyaluronic acid assay method utilizing cartilage protein it was possible to determine μg amounts of the substance. The method was based on the phenomenon that if reaction mixtures of a predetermined amount of proteoglycan mixed with increasing amounts of hyaluronic acid were subjected to gel chromatography then one would find a linear increase in the relative amount of hyaluronic acid (measured as uronic acid) in the voids (5). In the case of alternative methods published later it has been possible to get down as far as to ng levels. This has been achieved by means of using hyaluronic acid bound to an insoluble phase (so-called solid phase) for competition with (=inhibition by) hyaluronic acid present in a sample in respect of (=in its reaction with) an iodine-labelled fragment of proteoglycan containing HABr, iodine-labelled link protein, iodine-labelled mixtures thereof, or with non-labelled hyaluronectin (followed by labelled antibodies). In that case the amount of labelled reactant which is being bound to the solid phase will—if the amounts are chosen appropriately—give an indication of the amount of hyaluronic acid in the sample (2, 4, 7, 8, 10, 11, 12, 15). Hyaluronic acid has also been detected immunohistochemically by the use of hyaluronectin (16).

In view of the fact that the antigenic structures of HABr are altered upon binding to hyaluronic acid Thonar et al. (14) have suggested that this phenomenon should be exploited for measuring hyaluronic acid in the ng range. Their system relies on utilizing a plurality of reactants such as HABr in two forms (soluble and bound to solid phase) and antibodies directed against HABr determinants the exposure of which will depend on whether or not the hyaluronic acid binds to the HABr. Poole et al. (9) have proposed digestion with the aid of an enzyme exclusively degrading hyaluronic acid, followed by immunologic quantification of the hyaluronic acid fragments thus obtained.

There are thus a great number of methods available for quantitating extremely low levels of hyaluronic acid. At the same time, clinical interest directed towards measuring ng levels of hyaluronic acid is also potentially quite high, e.g. as regards such measurements in blood plasma, lymph, serum and urine. In spite of this situation, a commercially useful method has not been available up to now, the principal reason for this being that demands as regard the standard of such methods are much higher than in the case of a test to be used by just one small group of people in just one laboratory. Applicant has been endeavoring for a nubmer of years to develop a commercial test for hyaluronic acid. In the course of these endeavors, it has been found that the reaction between hyaluronic acid binding protein and hyaluronic acid is considerably more sensitive than might be gathered from scientific publications in this field. Quite surprisingly we have found i.a. (1) that one and the same batch of the recommended iodine-labelled mixture of HABr/link protein will give very different and entirely unacceptable measuring results from one single sample, (2) that the reaction between HABr and hyaluronic acid is considerably more sensitive to pH variations than could be inferred from earlier studies, and (3) that temperature dependence has been such that temperatures exceeding a certain degree should be avoided.

The invention duly heeds the difficulties inherent in these known methods for determining hyaluronic acid in biological and water-containing samples. The prior art methods in question are all so-called inhibition methods. They are based on the expedient that in addition to the hyaluronic acid of the sample at least one reactant possessing hyaluronic acid structure (reactant 1=derivatized hyaluronic acid=hyaluronic acid analogue) plus a second reactant possessing a hyaluronic acid binding structure (reactant 2) are reacted with each other so as to form a complex in which the reactants (1) and (2) are bound to each other due to biospecific affinity. Features especially characteristic of the invention reside in that (i) the reactant (2) employed is a reactant possessing that hyaluronic acid binding structure which is present in cartilage proteoglycan (=HABr) and (ii) the reaction of reactants (1) and (2) with each other is conducted at (a) a pH in the range of 5.5–7.4, this pH having been obtained in that externally added buffering components (buffer system acid—base pair) having a buffering capacity within the said pH range of a $>0.04$ M total concentration in the reaction mixture, and (b) a temperature in the range of $+0°$ C. to $+27°$ C.

The invention is adapted in particular for measuring serum samples. The term "externally added buffering components" means that these components have been added for neutralizing alkaline and/or acidic components carried along in the sample from its origin. Usually they are acid—base pairs having $pK_a$ values within the range of 5.0–7.9.

Inhibition methodology is well known to persons skilled in the art, and fundamentally the same methodology that is utilized in accordance with this invention is employed also within the field of immunochemical assays. Therefore, to a person skilled in the art upon having become acquainted with the difficulties as now revealed with respect to the hyaluronic acid assay methods in question it will be an easy task to construct inhibition systems to which the invention is applicable. In the case of the present invention the hyaluronic acid (analyte) is made to compete with a hyaluronic acid derivative (analog) for a hyaluronic acid binding structure on a protein. The amounts of reactants (1) and (2) are chosen such that the amount of the resultant complex and the amounts of uncomplexed reactant (1) or (2) will always be a measure of the amount of hyaluronic acid in the sample. A feature utilized by the invention in some way or other resides in having at least one reactant provided with an analytically detectable group. This may, but need not, be either reactant (1) or reactant (2); alternatives being detection systems utilizing so-called labelled antibodies or labelled anti-antibodies. Cp. for example Delpech et al. (2) using antihyaluronectin antibodies.

According to the most preferred embodiment of the invention the sample is preincubated with reactant (2) before reactant (1) is added.

Methods contemplated may be classified according to the marker systems employed (that is, according to the type of analytically detectable group). Thus there are enzyme, fluorescence, chemiluminescence, enzyme-substrate, isotope etc marker methods. In the case of some markers, their activity is altered considerably when the reactant to which such a marker is bound binds to its biospecific counterpart, i.e. is integrated into the complex. The activity of the marker in the reaction mixture will then become a function of the amount of complex formed and can be correlated directly with the amount of analyte—in our case hyaluronic acid. Measuring methods are usually called "homogeneous" if the activity of the marker is measured directly in the reaction mixture without previous physical separation of the complex from that labelled reactant which has not been incorporated in the complex. These "homogeneous" methods may be contrasted with "heterogeneous" methods where one does proceed to separation. Classification thus may also be based on whether a method is homogeneous or heterogeneous.

Among the heterogeneous methods there are various so-called precipitation methods involving as a first step complex formation in a homogeneous phase and in the next stage precipitation of the complex with a suitable precipitating agent. The precipitating agent may consist of precipitating, insolubilized or insolubilizable antibodies directed against some unlabelled reactant incorporated in the complex. Alternatively, the agent may be of a non-immunologic character. In another type of heterogeneous methods, either the analyte analogue or the biospecific counterpart capable of binding to an epitope that is common to both the analyte and the analyte analogue is bound to solid phase.

Reactant (1)

It is well known from earlier literature that hyaluronic acid fragments binding to HABr must comprise at least 10 monosaccharide units; therefore, in the present application and claims the term "hyaluronic acid structure" means that in reactant (1) there has to be a hyaluronic acid fragment of at least 10 monosaccharide units, preferably more than about 20 such units. Reactant (1) is a hyaluronic acid derivative (hyaluronic acid analog) that may be labelled, e.g. tritiated or labelled with $C^{14}$, or may be bound covalently, ionically or biospecifically to a polymer which is insoluble in the reaction medium contemplated. Especially in various affinity contexts the reducing end of the hyaluronic acid or the carboxyl groups thereof have been utilized for covalent coupling to adsorbents containing amino groups (13). These coupling methods may advantageously be utilized by the present invention, although in our case it has been found that the best procedure is to use the CNBr method, which is a well-established technique (1, 6).

Reactant (2)

An HABr suitable for the invention should be free from link protein and can be produced in a manner known per se (13). In the light of what is known at present it is most preferred, as in the prior art methods, to use the cartilage proteoglycan fragment obtained when the protein peptide segments rich in chondroitin and keratan sulfate are removed by means of trypsin digestion or with the aid of some other suitable enzyme that leaves the hyaluronic acid binding structure intact. This does not exclude the possibility of using also the intact proteoglycan monomer, optionally after removal of the chondroitin and keratan sulfate chains therefrom. The HABr may be derivatized in a manner such as is common in the case of proteins; thus the HABr may be adsorbed or covalently bound to a phase which is insoluble in the reaction medium or the HABr may be conjugated to any of a number of different analytically detectable groups (labelling). For labelling the proteoglycan it is advantageous to attach the label to the purified protein without the presence of the link protein.

Other Affinity Reactants

In the case of some of the inhibition methods contemplated, neither reactant (1) nor reactant (2) has an analytically detectable group. The complex or an uncomplexed unlabelled reactant may in such cases be quantified with antibodies directed against a suitable reactant. Thus if reactant (2) is unlabelled and soluble it is possible to employ antibodies which are directed against reactant (2). The preparation and selection of suitable antibodies will be performed in a manner such as is common practice for antibodies in general, using an immunogen that comprises such antigenic structures as are present in reactant (2), e.g. in the HABr.

pH Dependence

We have found that the reaction(s) between hyaluronic acid structure and HABr is/are most independent of the pH within the range of 5.8–7.3. In view of the fact that in aqueous samples of biological origin the pH may vary considerably, the demands on the externally added buffer are high: The buffer has to have sufficient buffer capacity to be able to buffer substantially every sample of the type contemplated, e.g. every urine, blood, plasma or serum sample, to a pH within the range of 5.8–7.3. Among the buffer systems we have tried up to now for serum samples, the only really good ones are $H_2PO_4^-/HPO_4^{2-}$ set to a pH in the range 5.8–7.3 which is below the pKa of $H_2PO_4^-$, the total concentration of added buffering components, for example phosphate, having been >0.04 M as e.g. >0.06 M or >0.1 M. Of course this does not exclude the possibility of using some other buffer system in these concentration ranges which are capable of buffering samples to the aforesaid range. For instance in the case of acidic samples one may want to use the $H_2PO_4^-/HPO_4^{2-}$ system set to a pH just above the pKa of $H_2PO_4^-$.

It goes without saying that all the types of additives employed must be such that they will not substantially interfere with the desired reactions.

Temperature

The reaction between HABr and hyaluronic acid structures is highly dependent on temperature and should not be carried out at a temperature above about +27° C. The practical lower limit is +0° C. The preferred range is +4° C. to +25° C., e.g. +4° C. to +22° C.

The invention also comprises a reagent kit to be employed for hyaluronic acid determination as set forth above and containing a hyaluronic acid derivative (reactant (1)), a second reactant possessing the hyaluronic acid binding structure of cartilage proteoglycan (reactant (2), HABr), and a buffer system capable of buffering the reaction mixtures obtained if reactant (1), reactant (2) and the type of sample contemplated are mixed with each other for the assay. In this reagent kit reactant 1 and 2 are packed in separate containers. For further information about the individual components, see above.

The invention is further defined in the attached claims and will now be illustrated by way of patent examples.

Reagents (Percentages are W/V Unless Otherwise Stated)

Kathon ® is an antimicrobial substance produced by Rohm & Haas, Philadelphia, USA.
Hyaluronic acid (=HA) was Healon ® from Pharmacia AB, Uppsala, Sweden,
BSA=bovine serum albumin
Sephacryl ® S-200=gel chromatography medium from Pharmacia AB, Uppsala, Sweden.
Tween ® is a detergent from Hefti, Zürich, Switzerland.
Standards: These were prepared by dilution of hyaluronic acid, Healon ®, in 0.05 M phosphate buffer pH 7.4 (containing 6% BSA, 0.1% Tween ®20, 0.15% Kathon ® and 0.9% NaCl) to 1 000, 500, 200, 75, 25, 10 μg/1. The said buffer was used as the 0 standard.
HA - agarose: This was prepared in that 70–75 mg of hyaluronic acid (Healon ®) were bound covalently to 10 g of agarose particles of particle size <5 um (Pharmacia AB). Coupling was effected at pH 10–10.5 by means of CNBr method according to Axén et al. (1) modified according to Kohn et al. (6).
Cartilage proteoglycan: The hyaluronic acid binding fragment thereof (HABr fragment), link protein and mixtures of these were prepared as described by Tengblad, A. (11, 12, 13).
Iodinations of proteins were performed as described by Tengblad (11, 12).

Test Variants

Variant (1) (prior art technique as regards labelled substance)

100 μl standard/sample, 100 μl HA bound to agarose (0.4 μl gel/ml in 0.05 M sodium phosphate buffer containing 1.65 M NaCl, 1% BSA, 0.1% Tween ® 20, 0.15% Kathon ®, pH 7.0) and 25 μl of a chloramine T iodinated mixture of HABr fragment and link protein diluted to 30 μg/l in the buffer as aforesaid bu with 6% BSA. All this is mixed and incubated for 3 hours at room temperature (18°–25° C.) unless stated otherwise. Wash 3×2.5 with 0.9% NaCl, 0.07% Tween ®.

Variant (2) (invention)

100 μl standard/sample and 200 μl of chloramine T iodinated pure HABr fragment diluted to 15 μg/l in 0.1 M phosphate buffer containing 1% BSA, 0.1% Tween ® 20, 0.15% Kathon ®, pH 6.1, are mixed and incubated for 60 minutes at room temperature (18°–22° C.) unless stated otherwise. Next 100 μl of HA bound to agarose particles (0.6 μl gel/l in the same buffer) are added, and the mixture is then incubated for 45 minutes at room temperature (18°–22° C.) unless stated otherwise. Wash 2×2 ml with 0.9% NaCl, 0.07% Tween ® 20.

EXAMPLE 1

One single mixture of HABr fragment and link protein was iodinated on two occasions. Two sera were tested with both materials in several tests run according to Variant (1). Results:

TABLE 1A

|  |  | Iodination (1) | Iodination (2) |
|---|---|---|---|
| Serum 1 | Concentration, average | 50 μg/l | 19 μg/l |
|  | Interassay, variation | 34% | 32% |
| Serum 2 | Concentration, average | 121 μg/l | 78 μg/l |
|  | Interassay, variation | 26% | 17% |

Pure HABr was iodinated on two occasions. Two sera were tested according to Variant (2) in several runs. Results:

TABLE 1B

|  |  | Iodination (1) | Iodination (2) |
|---|---|---|---|
| Serum 1 | Concentration, average | 38 μg/l | 38 μg/l |
|  | Interassay, variation | 5.5% | 6.1% |
| Serum 2 | Concentration, average | 112 μg/l | 104 μg/l |
|  | Interassay, variation | 9.3% | 4.0% |

EXAMPLE 2

A mixture of HABr fragment and link protein was iodinated and separated on Sephacryl ® S-200. A number of serum samples were tested in an assay in which the iodinated HABr fraction was employed as a tracer, and furthermore in an assay in which the iodinated link protein was employed as a tracer. Variant (1). Both runs, carried out in parallel, utilized the same standard and agarose-bound HA (0.2 μl/ml). Results:

TABLE 2

| Serum | Concentration, μg/l | |
|---|---|---|
| | $^{125}$I-HABr | $^{125}$I-link protein |
| TL | 46 | 133 |
| AS | 21 | 169 |
| C | 25 | 122 |
| A | 12 | 57 |
| N95 | 36 | 100 |
| N96 | 27 | 76 |
| N527 | 44 | 127 |
| N532 | 116 | 236 |
| N542 | 39 | 37 |
| N543 | 35 | 6.7 |
| N544 | 16 | 9.4 |
| N545 | 25 | 9.7 |
| N546 | 37 | 29 |
| N547 | 34 | 38 |
| N548 | 26 | 12 |
| N550 | 123 | 194 |

The experiments showed that different items are measured by link protein on one hand and HABr on the other hand.

EXAMPLE 3

Binding $B_o/T$ in % (that is, binding of 0 standard/total radioactivity added). Temperature dependence and kinetics.

TABLE 3A

| Temp | Variant (1) | Variant (2) |
|---|---|---|
| +4° C. | | 26.5% |
| +8° C. | 13.5% | |
| +18° C. | | 30.5% |
| +20° C. | 17.2% | |
| +23° C. | | 30.7% |
| +26° C. | 17.5% | |
| +30° C. | | 29.5% |
| +37° C. | 11.6% | 26.1% | that is, higher degree of binding and less dependence on temperature. The variation range (not given here) showed a temperature dependence which made it seem advisable to run the assay below a temperature of 27° C., preferably below 25° C., e.g. below 22° C.

TABLE 3B (Temp 23–26° C.)

| Variant (1) | | Variant (2) | | |
|---|---|---|---|---|
| Incubation Time | Binding | Incubation time | | Binding |
| | | 1st inc. | 2nd inc. | |
| 1 h | 12.8% | 0.5 h | | 32.3% |
| 2 h | 15.9% | 1 h | 0.75 h | 31.8% |
| 3 h | 17.5% | 2 h | | 31.3% |
| 5 h | 19.9% | | | |
| | | | 0.5 h | 27.9% |
| | | | 0.75 h | 31.6% |
| | | 1 h | 1.0 h | 33.3% |
| | | | 1.25 h | 33.8% |

EXAMPLE 4 pH in reaction mixture (I) and binding (B/T) expressed as % (II) for serum and standard respectively resulting from different pH-values of the buffer used.

100 μl standard or serum+100 μl of agarose-bound HA+100 μl av $^{125}$I-HABr in 0.1 M phosphate buffer, 1.0 M NaCl, 1% BSA, 0.1% Tween 20, 0.15% Kathon ®. The pH of the buffer was varied. Results:

TABLE 4

| pH in buffer used | pH obtained in the reaction mixture | | B/T obtained | |
|---|---|---|---|---|
| | Standard | Sample | Standard | Sample |
| 4.0 | 5.5 | 5.5 | 9.3 | 8.6 |
| 5.0 | 5.8 | 5.8 | 9.7 | 9.2 |
| 6.0 | 6.3 | 6.5 | 11.3 | 10.8 |
| 6.5 | 6.7 | 6.8 | 11.4 | 10.9 |
| 6.8 | 6.9 | 7.3 | 11.7 | 11.3 |
| 7.2 | 7.2 | 7.9 | 12.0 | 11.0 |
| 7.5 | 7.4 | 8.1 | 12.0 | 10.0 |
| 7.8 | 7.5 | 8.3 | 11.1 | 9.5 |
| 8.0 | 7.6 | 8.5 | 10.6 | 8.8 |

The results show that a pH in the range of 5.8 to 7.4 should be chosen. The difficulties are due to the pH variations and great buffer capacity normally found in serum samples.

References

1. Axén R. et al (Pharmacia AB)
   U.S. Pat. No. 3,645,852
2. Delpech B. et al
   Anal Biochem 149 (1985) p. 555–65
3. Engström-Laurent A.
   Thesis 1985, Department of Internal Medicine, University Hospital, and Department of Medical and Physiological Chemistry, BMC, Uppsala university, Sweden
4. Engström-Laurent A. et al
   Scand J Clin Lab Invest 45 (1985) p. 497–507
5. Hardingham T. E. et al
   Biochem J 159 (1976) p. 143–147
6. Kohn J. et al
   Biochem Biophys Res Commun 107 (1982) p. 878–
7. Laurent U. B. G.
   Exp Eyes Res 33 (1981) p. 147–55
8. Laurent U. B. G. et al
   Anal Biochem 109 (1980) p. 386–94
9. Poole A. R. et al
   J Biol Chem 260 (1985) p. 6020–25
10. Tengblad A.
    Thesis 1981, Department of Medical and Physiological Chemistry, BMC, University of Uppsala, Sweden
11. Tengblad A.
    Biochem J 199 (1981) p. 297–305
12. Tengblad A.
    Biochem J 185 (1980) p. 101–5
13. Tengblad A.
    Biochim Biophys Acta 578 (1979) p. 281–9
14. Thonar J-M. et al
    J Biol Chem 257 (1982) p. 14173–14180
15. Lacy B. E. et al
    Anal Biochem 158 (1986) p. 436–42.
16. Girard N. et al
    J. Histochem Cytochem 34 (1986) p. 539–41.

We claim:

1. In a method for the determination of hyaluronic acid in a sample by means of an inhibition technique that includes the steps of
   (i) reacting the sample with a first reactant (1) possessing hyaluronic acid structure and a second reactant (2) possessing a hyaluronic acid binding structure to thereby form a complex in which reactants (1) and (2) are held together due to biospecific affinity, and (ii) determining the amount of hyaluronic acid in said complex by the use of a label attached covalently to one of said reactants or indirectly by the use of a labelled antibody reactive with said complex, the improvement comprising (A) using a reactant (2) that is free from link protein and which possesses the hyaluronic acid binding region of cartilage proteoglycan (HABr), and (B) reacting reactant (1) with reactant (2)

(a) at a pH within the range of 5.8–7.3, this pH having been obtained by adding buffering components having a buffering capacity within the pH range of 5.8–7.3, and having a total concentration exceeding 0.04 M in the reaction mixture, and (b) at a temperature in the range of 0° C. to 27° C.

2. A method in determining hyaluronic acid according to claim 1 wherein reactant (1) is hyaluronic acid bound to solid phase.

3. A method according to claim 1 wherein reactant (2) possesses an analytically detectable group.

4. A method according to claim 1 wherein the buffering components are $H_2PO_4^-/HPO_4^{2-}$.

5. A method according to claim 1 wherein the sample is preincubated with reactant (2) at said pH and said temperature before reactant (1) is added.

* * * * *